(12) United States Patent
Johansson et al.

(10) Patent No.: US 11,740,759 B2
(45) Date of Patent: Aug. 29, 2023

(54) DISPLAY DEVICE AND INTERFACES FOR CRYOGENIC DEVICES

(71) Applicant: Pacira CryoTech, Inc., Parsippany, NJ (US)

(72) Inventors: Eric Theodore Johansson, Dublin, CA (US); Jeff Gamelsky, Palo Alto, CA (US); Pierre-Andre Mugnier, Moss Beach, CA (US)

(73) Assignee: Pacira CryoTech, Inc., Parsippany, NJ (US)

( * ) Notice: Subject to any disclaimer, the term of this patent is extended or adjusted under 35 U.S.C. 154(b) by 107 days.

(21) Appl. No.: 17/096,491

(22) Filed: Nov. 12, 2020

(65) Prior Publication Data

US 2021/0157472 A1 May 27, 2021

Related U.S. Application Data

(60) Provisional application No. 62/940,985, filed on Nov. 27, 2019.

(51) Int. Cl.
| | |
|---|---|
| *G06F 3/04817* | (2022.01) |
| *A61F 7/12* | (2006.01) |
| *G06F 3/0485* | (2022.01) |
| *G06F 3/0346* | (2013.01) |
| *A61F 7/00* | (2006.01) |

(52) U.S. Cl.
CPC ........... *G06F 3/04817* (2013.01); *A61F 7/12* (2013.01); *G06F 3/0346* (2013.01); *G06F 3/0485* (2013.01); *A61F 2007/0093* (2013.01); *A61F 2007/126* (2013.01)

(58) Field of Classification Search
None
See application file for complete search history.

(56) References Cited

U.S. PATENT DOCUMENTS

| | | |
|---|---|---|
| 7,713,266 B2 | 5/2010 | Elkins et al. |
| 7,850,683 B2 | 12/2010 | Elkins et al. |
| (Continued) | | |

FOREIGN PATENT DOCUMENTS

CN 203153935 8/2013

OTHER PUBLICATIONS

Author: Fitbit. Title: Fitbit Charge 2: How to Charge Your Tracker. Publication Date: Oct. 28, 2016. URL: https://www.youtube.com/watch?v=M7W05IqKkP0.*

*Primary Examiner* — Matthew Ell
*Assistant Examiner* — David V Luu
(74) *Attorney, Agent, or Firm* — Kilpatrick Townsend & Stockton LLP

(57) ABSTRACT

The disclosure describes a cryogenic device with a display device for displaying one of a plurality of user-interfaces associated with a plurality of cryogenic device states. The cryogenic device is configured to: generate an initial user-interface for display on the display device; determine that the cryogenic device is in a first state; generate, in response to determining that the cryogenic device is in the first state, instructions for rendering a first user-interface, wherein the first user-interface is associated with the first state; and cause the display device to display the first user-interface. In this way, the cryogenic device may have a dynamic user interface that is configured to response to states of the cryogenic device.

28 Claims, 10 Drawing Sheets

(56) References Cited

U.S. PATENT DOCUMENTS

| | | |
|---|---|---|
| 7,998,137 B2 | 8/2011 | Elkins et al. |
| 8,298,216 B2 | 10/2012 | Burger et al. |
| 8,409,185 B2 | 4/2013 | Burger et al. |
| 8,461,108 B2 | 6/2013 | Hsu et al. |
| 9,039,688 B2 | 5/2015 | Palmer, III et al. |
| 9,066,712 B2 | 6/2015 | Reynolds et al. |
| 9,072,498 B2 | 7/2015 | Elkins et al. |
| 9,241,753 B2 | 1/2016 | Fourkas et al. |
| 9,254,162 B2 | 2/2016 | Burger et al. |
| 9,295,512 B2 | 3/2016 | Allison et al. |
| 9,314,290 B2 | 4/2016 | Fourkas et al. |
| 9,345,526 B2 | 5/2016 | Elkins et al. |
| 9,610,112 B2 | 4/2017 | Karnik et al. |
| 9,668,800 B2 | 6/2017 | Karnik et al. |
| 10,016,229 B2 | 7/2018 | Carnell et al. |
| 10,085,789 B2 | 10/2018 | Carnell et al. |
| 10,085,881 B2 | 10/2018 | Karnik et al. |
| 10,130,409 B2 | 11/2018 | Hinton et al. |
| 10,314,739 B2 | 6/2019 | Allison et al. |
| 10,470,813 B2 | 11/2019 | Allison et al. |
| 10,596,030 B2 | 3/2020 | Karnik et al. |
| 10,888,366 B2 | 1/2021 | Allison |
| 2010/0047745 A1* | 2/2010 | Bergqwist ............. G16H 20/60 707/769 |
| 2011/0202048 A1 | 8/2011 | Nebrigic |
| 2012/0089211 A1 | 4/2012 | Curtis et al. |
| 2012/0259322 A1 | 10/2012 | Fourkas et al. |
| 2014/0276539 A1 | 9/2014 | Allison et al. |
| 2014/0303608 A1 | 10/2014 | Taghizadeh |
| 2015/0304478 A1* | 10/2015 | Kim ...................... G16H 40/63 455/414.3 |
| 2015/0351822 A1* | 12/2015 | Mulcahey .......... A61B 18/0218 606/22 |
| 2016/0082192 A1* | 3/2016 | Veasey .................. G16H 40/63 604/211 |
| 2016/0266742 A1* | 9/2016 | Hussain ............... G06F 3/04842 |
| 2016/0361553 A1* | 12/2016 | Kaula ................ A61N 1/36014 |
| 2017/0040553 A1* | 2/2017 | Watabe ................ H01L 51/0085 |
| 2017/0147192 A1* | 5/2017 | Keegan ............... G06F 3/04817 |
| 2018/0116705 A1 | 5/2018 | Lee et al. |
| 2019/0038459 A1 | 2/2019 | Karnik et al. |
| 2019/0142494 A1 | 5/2019 | Cross et al. |
| 2020/0034033 A1* | 1/2020 | Chaudhri ................ H04L 51/18 |
| 2020/0097226 A1* | 3/2020 | Niiyama ............... G06F 3/1259 |
| 2021/0128220 A1* | 5/2021 | Baust ................. A61B 18/1492 |

\* cited by examiner

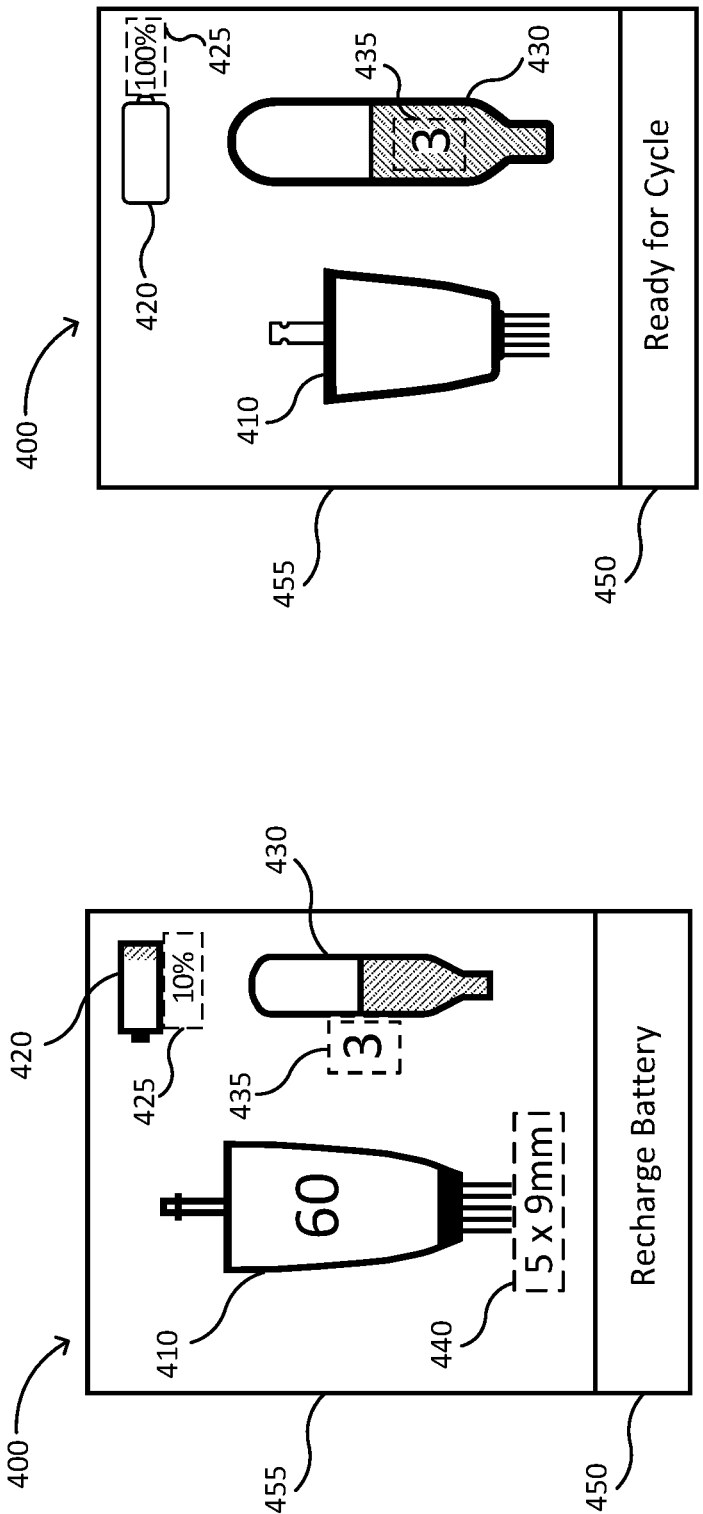

DISPLAY DEVICE AND INTERFACES FOR CRYOGENIC DEVICES

CROSS REFERENCE TO RELATED APPLICATION DATA

The present application claims the benefit of U.S. Provisional Appln No. 62/940,985 filed Nov. 27, 2019; the full disclosure which is incorporated herein by reference in its entirety for all purposes.

RELATED FIELDS

Devices, systems, and methods for cooling tissue for therapeutic purposes, including nerves for treating pain.

BACKGROUND

The present disclosure is generally directed to medical devices, systems, and methods for cryotherapy. More specifically, the present disclosure relates to a cryogenic device for cryogenically cooling target tissues of a patient so as to degenerate, inhibit, remodel, or otherwise affect a target tissue to achieve a desired change in its behavior or composition. Cryogenic cooling of neural tissues has been shown to be effective in treating a variety of indications including pain (e.g., occipital and other neuralgias, neuromas, osteoarthritis pain), spasticity, and joint stiffness, among others. For example, cooling neural tissues has been found to degenerate or inhibit nerves that are instrumental in causing these conditions. Cryogenic cooling has also been employed to address cosmetic conditions, for example, by inhibiting undesirable and/or unsightly effects on the skin (such as lines, wrinkles, or cellulite dimples) or on other surrounding tissue.

In light of the above, cryogenic devices with needle probes have emerged as a mode of therapeutically cooling target tissues for treating a variety of indications. The needle probes of such devices are typically inserted into a patient's skin adjacent to a target tissue. Some cryogenic probes may include a cryogen that may be either injected into the target tissue via openings in needles of the needle probe, such that the target tissue is cooled directly by the cryogen. Other cryogenic probes may include closed needle tips, in which case the needles may be cooled (e.g., by a flow of the cryogen), and the target tissue adjacent to the cooled needles may thereby be cooled by conduction. Cryogenic probes have proved to be effective in creating cryozones within a patient at or around target tissues with precision, convenience, and reliability. A cryozone may be a volume of tissue that is cooled by one or more needles of a cryogenic probe (e.g., a volume of tissue near or around a distal portion of the needles). For example, a cryozone may be a volume of tissue that is cooled so as to freeze the tissue within the volume (e.g., the cryozone may be defined by an approximately 0° C. (or other suitable temperature) isotherm that may form around a needle of the cryogenic probe).

BRIEF SUMMARY

This disclosure relates to improved medical devices, systems, and methods. Many of the devices, systems, and methods described herein will be beneficial for cryotherapy using a cryogenic device.

In some embodiments, a cryogenic device may include a handpiece capable of being held by a user. The handpiece may include a cryogen pathway configured to conduct a cryogen toward a needle probe including one or more needles, wherein the cryogen may be configured to deliver cryotherapy to a target tissue via the one or more needles. The cryogenic device may include a display device configured to display one of a plurality of user-interfaces, the plurality of user-interfaces being associated with a plurality of cryogenic device states. The cryogenic device may also include a processor coupled to the display device. The processor may be configured to generate an initial user-interface for display on the display device. The processor may be configured to determine that the cryogenic device is in a first state. The processor may be configured to generate, in response to determining that the cryogenic device is in the first state, instructions for rendering a first user-interface, where the first user-interface is associated with the first state. The processor may be configured to cause the display device to display the first user-interface.

Implementations may include one or more of the following features. The display device may be disposed on the handpiece of the cryogenic device. The display device may be an LCD or OLED screen.

The first user-interface may include an icon field including one or more icons indicating information associated with the cryogenic device or a selected cryotherapy program. The first user-interface may further include a status element including a textual description of a status of the cryogenic device. The selected cryotherapy program may specify, for example, a desired cryozone volume and/or a number of treatment cycles. Further, in some instances the textual description may be scrolled through the status element or broken into smaller messages that are alternately displayed in sequence.

The plurality of cryogenic device states may include a cycle state, where the cycle state is associated with the cryogenic device preparing for or performing a particular cryotherapy cycle. The plurality of cryogenic device states may also include a charging state, where the charging state is associated with a battery of the cryogenic device being charged. The plurality of cryogenic device states may also include a standard state, where the standard state is associated with the cryogenic device being turned on and not in the cycling state or the charging state.

The cycle state may be associated with a cycle user-interface, where the cycle user-interface may include an enlarged progress element indicating a progress of a treatment cycle. The enlarged progress element may, for example, include a count-down timer (or a count-up timer). The cycle user-interface may further include a status element. The charging state may be associated with a charging user-interface, where the charging user-interface may include an enlarged battery indicator element. The standard state may be associated with a standard user-interface, where the standard user-interface may include one or more of a battery indicator element indicating a battery status, a probe descriptor element indicating information about the needle probe, a cryogen status indicator indicating an amount of usable cryogen in a current cryogen cartridge, a cycle counter element indicating a number of treatment cycles remaining or a number of treatment cycles performed with a current cryogen cartridge, and a status element for indicating a status of the cryogenic device.

The plurality of cryogenic device states may include an error state associated with an error user-interface, where the error user-interface may include a first portion including an icon indicating a particular error and a second portion including an enlarged status element indicating the particular error. The first portion and the second portion may be non-overlapping portions of the error user-interface.

The cycle user-interface and the standard user-interface may be in a first orientation, and the charging user-interface may be in a second orientation, the first orientation being different from the second orientation. For example, the first orientation may be a 180-degree rotation of the second orientation.

The processor may be further configured to receive data from one or more accelerometers of the cryogenic device. The processor may determine, based on the received data, an orientation of the cryogenic device. The processor may orient the first user-interface in a manner consistent with the determined orientation of the cryogenic device.

In some embodiments, one or more methods may be employed to display a dynamic user interface on the described cryogenic device. One such method may include, by a processor associated with the cryogenic device, generating an initial user-interface for display on a display device associated with the cryogenic device. The processor may determine that the cryogenic device is in a first state, where the first state is one of a plurality of cryogenic device states. The processor may generate, in response to determining that the cryogenic device is in the first state, instructions for rendering a first user-interface, where the first user-interface is associated with the first state and is one of a plurality of user-interfaces. The processor may cause the display device to display the first user-interface.

Another such method may include displaying an initial user-interface on a display device associated with the cryogenic device. The method may further include determining that the cryogenic device is in one of a plurality of cryogenic device states including a cycle state, a charging state, and a standard state. The method may include generating, in response to determining that the cryogenic device is in one of the plurality of cryogenic states, instructions for rendering one of a plurality of user-interfaces, the plurality of user-interfaces being associated with the plurality of cryogenic device states. The method may include causing the display device to display one of the plurality of user-interfaces

BRIEF DESCRIPTION OF THE DRAWINGS

FIGS. 4A-4B illustrate two example standard user-interfaces, which may be associated with a standard state of the cryogenic device.

DETAILED DESCRIPTION

The present disclosure describes display interfaces to be used in association with cryogenic devices that may be used to deliver a cryotherapy to patients. In some embodiments, the described cryogenic devices may include needles for delivering cryotherapy subcutaneously to target particular tissues for treating a variety of conditions. For example, the cryogenic devices may include needles that are configured to be inserted near peripheral nerves to deliver cryotherapy to the peripheral nerves to treat pain, spasticity, or other such conditions that may be improved by such therapy. More information about the use of cryotherapy for alleviation of pain or spasticity, may be found in U.S. Pat. No. 8,298,216 filed Nov. 14, 2008; U.S. Pat. No. 9,610,112 filed Mar. 18, 2014; U.S. Pat. No. 10,085,789 filed Mar. 13, 2017; and U.S. Patent Publn No. 2019/0038459 filed Sep. 14, 2018, the full disclosures of which are incorporated herein by reference in their entirety for all purposes. The cryogenic devices may also be used for prophylactic treatment such as disruption or prevention of neuromas, for example, as described in U.S. Pat. No. 10,470,813 filed Mar. 14, 2016, the full disclosure of which is incorporated herein by reference in its entirety for all purposes.

As cryotherapy has become more prevalent and as its therapeutic effects have become realized for a number of indications, improvements to cryogenic devices to facilitate the use of such devices, and thereby enhance cryotherapy, have become necessary. In particular, user interfaces provided by current cryogenic devices are often lacking in that they do not effectively convey relevant information to operators of such devices, and as such may result in non-optimal use by the operators. The user interfaces are often not intuitive and may not present information in an accessible manner, sometimes causing even well-trained operators to misunderstand or disregard relevant information that the cryogenic devices may be trying to communicate. To address this problem, the present disclosure provides improved user interfaces for a cryogenic device that displays information effectively and intuitively.

Figure 1:
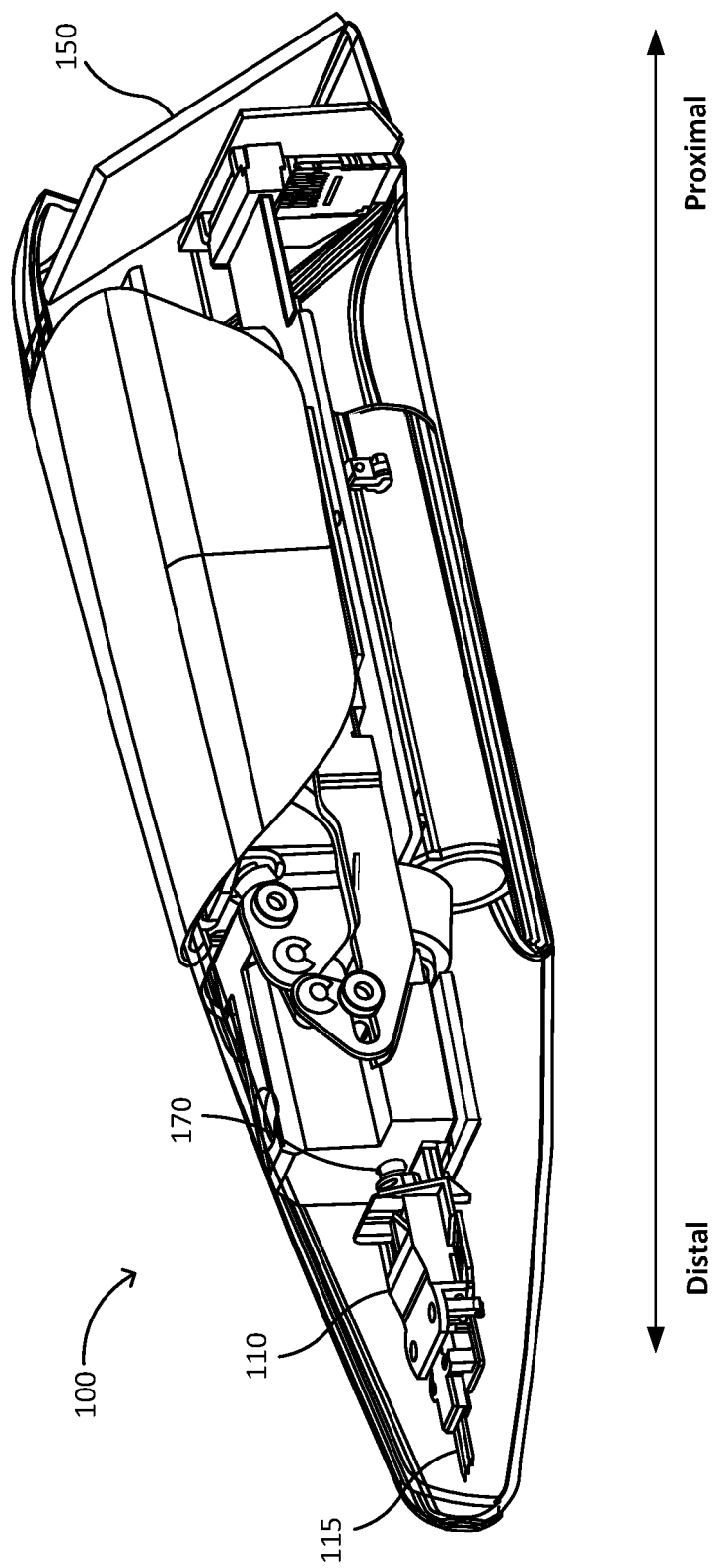
FIG. 1 illustrates an example embodiment of a cryogenic device including a needle probe having one or more needles.

FIG. 1 illustrates an example embodiment of a cryogenic device 100 including a needle probe 110 having one or more needles 115. As shown in the illustrated example embodiment, the cryogenic device 100 may be a self-contained handpiece suitable for being grasped and manipulated by an operator's hand. In other embodiments, the cryogenic device may include physically separated components. For example, the cryogenic device may include a handpiece including a needle probe and a cryogen cartridge that is separated from the handpiece. In some embodiments, the cryogen cartridge 130 may be a disposable cartridge filled with a cryogen (e.g., nitrous oxide, fluorocarbon refrigerants, and/or carbon dioxide). In some embodiments, as illustrated in FIG. 1, the cryogenic device 100 may include a probe receptacle 170 configured to receive a needle probe 110. In some embodiments, the probe receptacle 170 may be configured to couple the needle probe 110 to a cryogen cartridge via a cryogen pathway (not illustrated).

Figure 2:
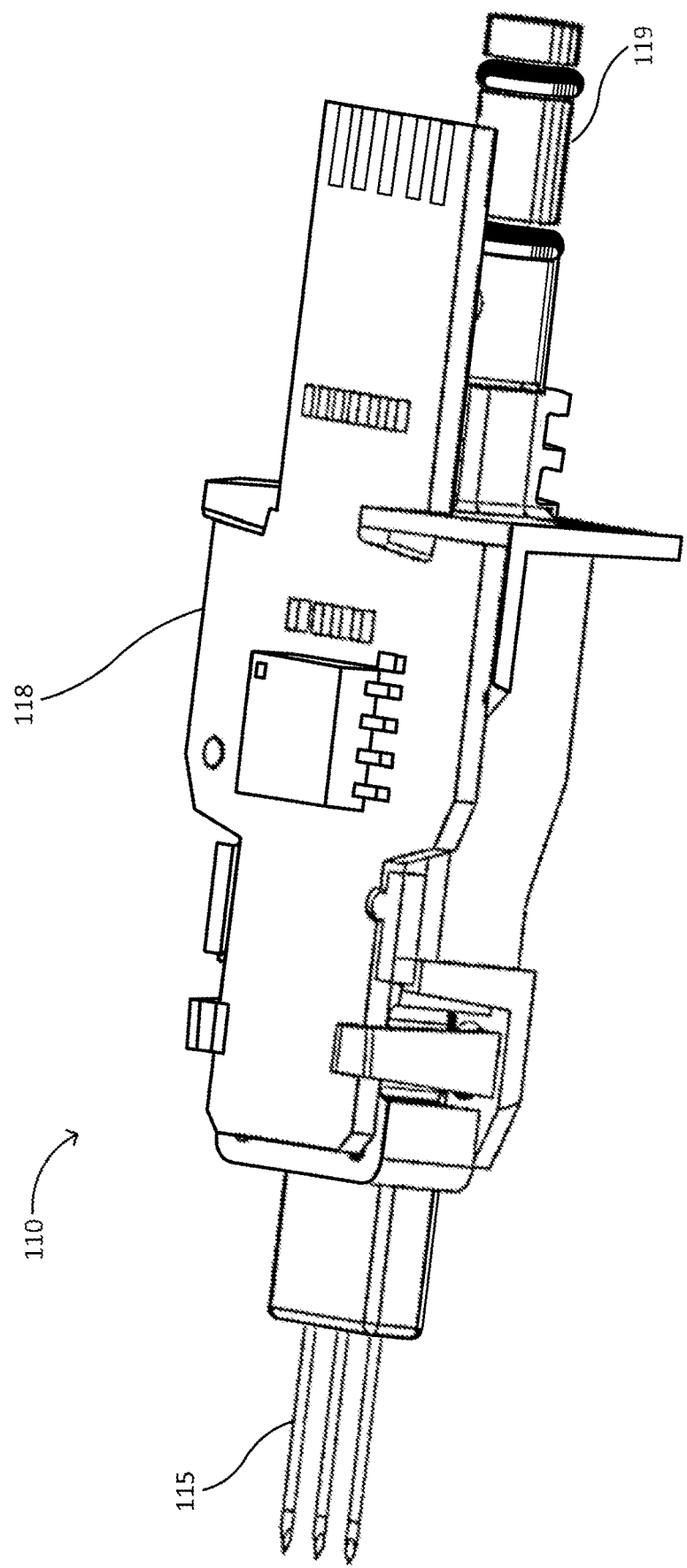
FIG. 2 illustrates an example needle probe.

FIG. 2 illustrates an example needle probe 110. In some embodiments, the needle probe 110 may include one or more needles 115 suited for penetration into a patient's skin adjacent to a target tissue (e.g., nerve tissue). For example, as illustrated in FIG. 2, the needle probe 110 may include three needles 115. Each of the needles of the needle probe 110 may have needle lumens disposed therein (not illustrated). In some embodiments, the needles 115 may have closed tips without any distal openings, such that they do not allow for the ejection of cryogen from the distal end of the needles 115. In these embodiments, the needles 115 themselves are cooled and adjacent tissue is thereby cooled by conduction. In some embodiments, the needle probe 110 may include a probe extension 119 that is configured to be securable to the probe receptacle 170. When the needle probe is secured to the probe receptacle, the probe extension extends proximally toward the proximal end of the cryogenic device. cryogen pathway (for illustrative purposes, proximal and distal directions are indicated in FIG. 1). Referencing FIG. 2, the probe extension 119 may have a probe lumen (not illustrated) disposed therein, the probe lumen being an elongate element that extends from a proximal end to a distal end. When the needle probe is secured to the probe receptacle, the probe lumen may be fluidically coupled to the cryogen pathway. The probe lumen may also be coupled to the needle lumens of the needles 115 at the distal end of the cryogenic device, such that a cryogen may be allowed to pass through the probe lumen and into the needle lumens (e.g., to cool the needle tips, which may then cool a target tissue to create a cryozone).

In some embodiments, the one or more needles 115 may be inserted into and beyond a skin of the patient such that distal portions of the needles 115 may be adjacent to a target tissue (e.g., nerve tissue). In some embodiments, once the needles 115 are positioned, an operator may submit an input to the cryogenic device 100 (e.g., by actuating a user-input button, tapping a user-interface element on a touchscreen, etc.) to cause a controller to open a supply valve, thereby enabling a cryogen to flow from a cryogen cartridge to lumens of the needles 115 via a cryogen pathway. The distal portions of the needles 115 may be cooled by the cryogen flow and may create a cooling zone around the target tissue.

In some embodiments, the cryogenic device 100 may be a smart device that includes a first processor (e.g., located within the handpiece and apart from the needle probe 110) to assist the operator with performing a treatment. In some embodiments, the needle probe 110 may be a smart probe. In these embodiments, the needle probe 110 may include a printed circuit board assembly (PCBA). The PCBA of the needle probe 110 may include an onboard processor. In some embodiments, the PCBA may also include a memory component. The PCBA may further include one or more connectors (e.g., a card edge connector) that electrically couple the needle probe 110 to the remainder of the cryogenic device 100 (e.g., the handpiece portion). For example, when a needle probe is received by the probe receptacle 170, a portion of the PCBA 118 may be received by a port in the handpiece portion.

Once the PCBA 118 of the needle probe 110 is connected to the handpiece portion, the needle probe 110 may be able to transmit and/or receive information to/from the handpiece portion (e.g., via its processor). In some embodiments, the needle probe 110 may transmit a probe descriptor that may, among other things, identify a corresponding probe type of the needle probe. For example, the probe descriptor may identify the number of needles (e.g., a single-needle probe, a three-needle probe, a five-needle probe), the lengths of needles, the configuration of needles (e.g., a rectangular array, a square array, elliptical, circular, triangular, a three-dimensional shape such as an inverted pyramid shape), or any other suitable characteristics of the needle probe. In these embodiments, the first processor may be further configured to determine, based on the received probe descriptor information, that the detachable needle probe is of a particular probe type of a plurality of probe types. In some embodiments, the probe descriptor may include information about the needle probe 110 that may be used to derive treatment-related information.

For example, the probe descriptor information may include an average cryogen flow rate for an associated needle probe 110, which may be used by the first processor (e.g., on the handpiece) to calculate an amount of cryogen that has been used and/or an amount that is remaining in the cryogen cartridge 130. The first processor may calculate these amounts based on the average cryogen flow rate and the amount of time a supply valve for releasing cryogen has been opened. As another example, needle dimensions, the number of needles, and other suitable parameters associated with the needle probe 110 may be used to derive cryogen flow amounts, cryogen amount used during a cycle, a cryogen amount remaining in a cartridge, and/or any other suitable treatment-related information. As another example, the probe descriptor information may include information that may be used by other treatment functionalities such as a skin warmer (e.g., a resistive heating element that is configured to be near or adjacent to the skin during treatment) that is configured to apply heat energy to a skin surface to reduce or prevent collateral tissue damage. In this example, a particular probe may send probe descriptor information that may be used to determine parameters for operating the skin warmer (e.g., power level, duration of heating, etc.).

More information about cryogenic devices with skin warmers may be found in U.S. Pat. No. 10,470,813 filed Mar. 14, 2016, which is incorporated herein by reference in its entirety for all purposes. Any of this information may be shown on any suitable user interface of display (e.g., in real-time as a treatment is being performed) associated with the cryogenic device 100 (e.g., an LCD screen of the cryogenic device 100). In some embodiments, a treatment recommendation may be determined and shown on the display. For example, a particular needle probe 110 may be associated with a particular type of treatment, and a treatment recommendation may thus be displayed based on a determination that the particular needle probe 110 has been inserted. An operator may then perform a treatment based on this recommendation.

In some embodiments, the probe descriptor may include "expiration" details of the needle probe 110 (e.g., the needle probe 110 may be configured to expire after a set number of treatment cycles for safety reasons). More information about smart cryogenic devices and smart probes may be found in U.S. Pat. No. 10,130,409 filed Nov. 20, 2018, which is incorporated by reference herein in its entirety for all purposes. As another example, the probe descriptor information may include information relating to parameters of treatment cycles generally or of different phases of treatment cycles associated with a cryotherapy that may be performed using the associated needle probe 110. An example treatment cycle may include a pre-treatment warming period during which a heating element is warmed, a cryogen delivery period during which cryogen is delivered to the one or more needles of the needle probe 110, and a recovery period following the cryogen delivery period during which cryogen is not delivered. In this example, the probe descriptor information for a particular needle probe 110 may specify a duration for each of these periods. More information about treatment cycles may be found in U.S. Patent Publn No. 2019/0038459 filed Sep. 14, 2018, which is incorporated herein by reference in its entirety for all purposes.

In some embodiments, the first processor may receive any other suitable information (e.g., from one or more sensors associated with the cryogen cartridge 130), such as the amount of cryogen remaining (or at least the available useful cryogen) within the cryogen cartridge 130 once it is positioned in a cartridge holder.

Figure 3A:
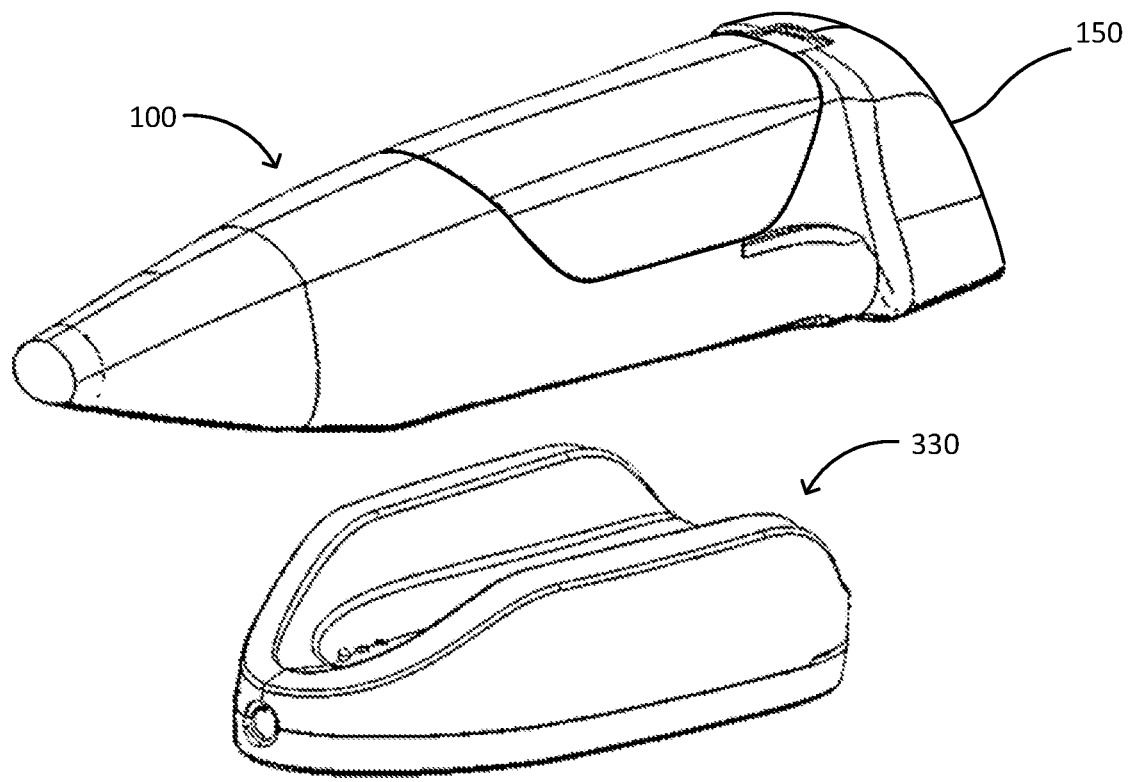
FIGS. 3A-3B illustrate an example embodiment of a cryogenic device being docked onto a charging device.
Figure 3B:
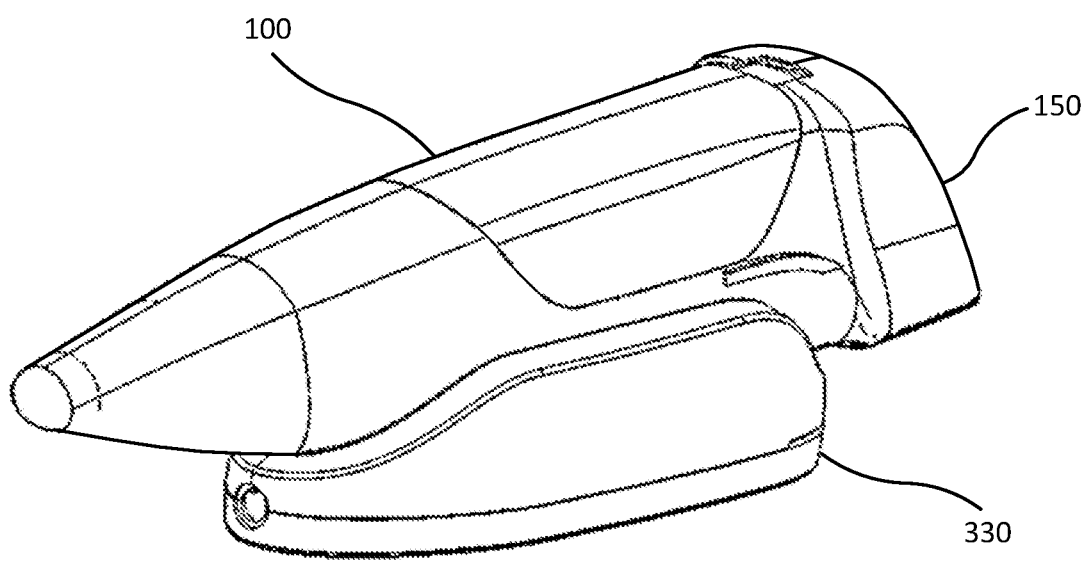

In some embodiments, the cryogenic device 100 may be rechargeable. For example, the cryogenic device 100 may include one or more rechargeable batteries that may be recharged by coupling the cryogenic device 100 to a charging device. FIGS. 3A-3B illustrate an example embodiment of a cryogenic device 100 being docked onto a charging device 330. As illustrated, the charging device 330 and the cryogenic device 100 may be shaped such that the cryogenic device 100 is adapted for being docked onto the charging device 330, which may charge the cryogenic device 100. In the illustrated example, the handpiece portion of the cryogenic device 100 is configured to rest substantially horizontally (or along an axis along which the cryogenic device extends) on a charging cradle formed by the charging device 330 to receive charging energy. The charging device 330 may be configured to be plugged into an electrical source. Alternatively or additionally, the charging device 330 may itself include one or more batteries that may be used to supply energy to the cryogenic device 100. In some embodiments, the charging device may be a wireless charger, and the cryogenic device 100 may be charged wirelessly when it is within range.

Figure 3C:
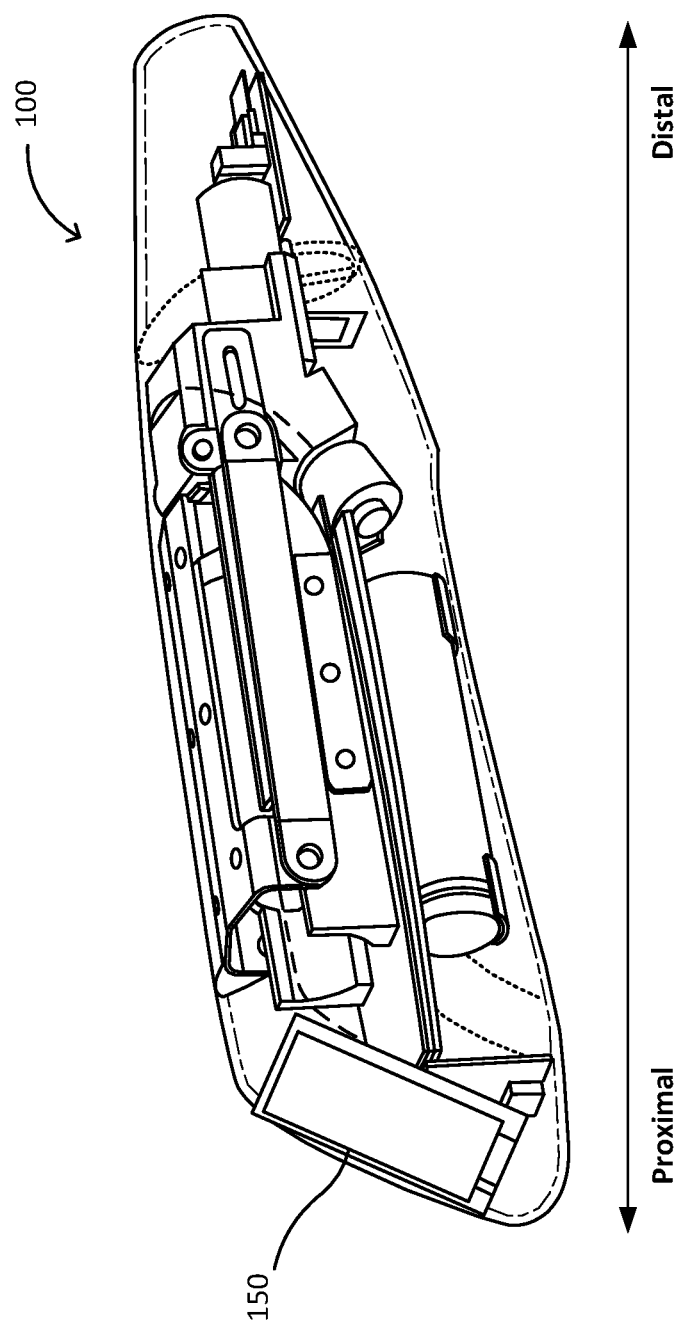
FIG. 3C illustrates a cryogenic device coupled to a display device, where the display device is mounted or otherwise disposed on the cryogenic device.

In some embodiments, the cryogenic device 100 may be coupled to a display device. FIG. 3C illustrates a cryogenic device 100 coupled to a display device 150 (e.g., an LCD screen, an OLED screen, etc.), where the display device 150 is mounted or otherwise disposed on the cryogenic device 100. In some embodiments, the display device 150 may display a user-interface that is capable of presenting a variety of relevant information to the operator before, during, and/or after treatment. For example, the display device 150 may present information about a needle probe 110 that is currently positioned within the probe receptacle 170 (e.g., information derived from a probe descriptor received from the needle probe 110, or any other suitable information described herein). This information may be presented in real-time as a treatment is being performed.

In some embodiments, the cryogenic device 100 may be associated with a plurality of cryogenic device states. These states may define a mode or condition of the cryogenic device 100 at a given time. For example, the cryogenic device 100 may be in a "cycle state." The cycle state may be associated with the cryogenic device 100 preparing for or performing a particular cryotherapy treatment cycle. Cryotherapy treatments may include one or more treatment cycles during which a tissue of a patient is cooled to effect a therapeutic benefit, with each treatment cycle lasting for a prescribed amount of time. As another example, the cryogenic device 100 may be in a "charging state." The charging state may be associated with a battery of the cryogenic device 100 being charged. As another example, the cryogenic device 100 may be in an "error state." The error state may be associated with a device condition where an error has been identified for the cryogenic device 100, rendering the cryogenic device 100 unusable or non-optimal. As another example, the cryogenic device 100 may be in a "stand-by state." The stand-by state may be associated with a power-saving mode, where the cryogenic device 100 may be ON, but many of its functions are turned off or throttled (e.g., the brightness of the display device 150 may be reduced). As another example, the cryogenic device 100 may be in a "standard state." The standard state may describe a condition where the cryogenic device 100 is ON and ready for use, without being associated with any other special conditions or modes. For example, the standard state may be associated with the cryogenic device 100 being turned ON and not in any of the other states (e.g., the cycling state, the charging state, the error state). Although particular states are described herein, the disclosure contemplates any suitable number of states associated with any suitable modes or conditions.

In some embodiments, the display device 150 may be configured to display one of a plurality of user-interfaces. Each of the plurality of user-interfaces may be associated with a plurality of cryogenic device states. For example, a particular user-interface may be associated with a particular state of the cryogenic device 100. As another example, a particular user-interface may be associated with a subset of states of the cryogenic device 100. Although particular user-interfaces are described herein, the disclosure contemplates any suitable number of user-interfaces associated with any suitable cryogenic device states. For example, the cryogenic device 100 may have different treatment modes, and these treatment modes may have different associated user-interfaces.

Figure 3D:
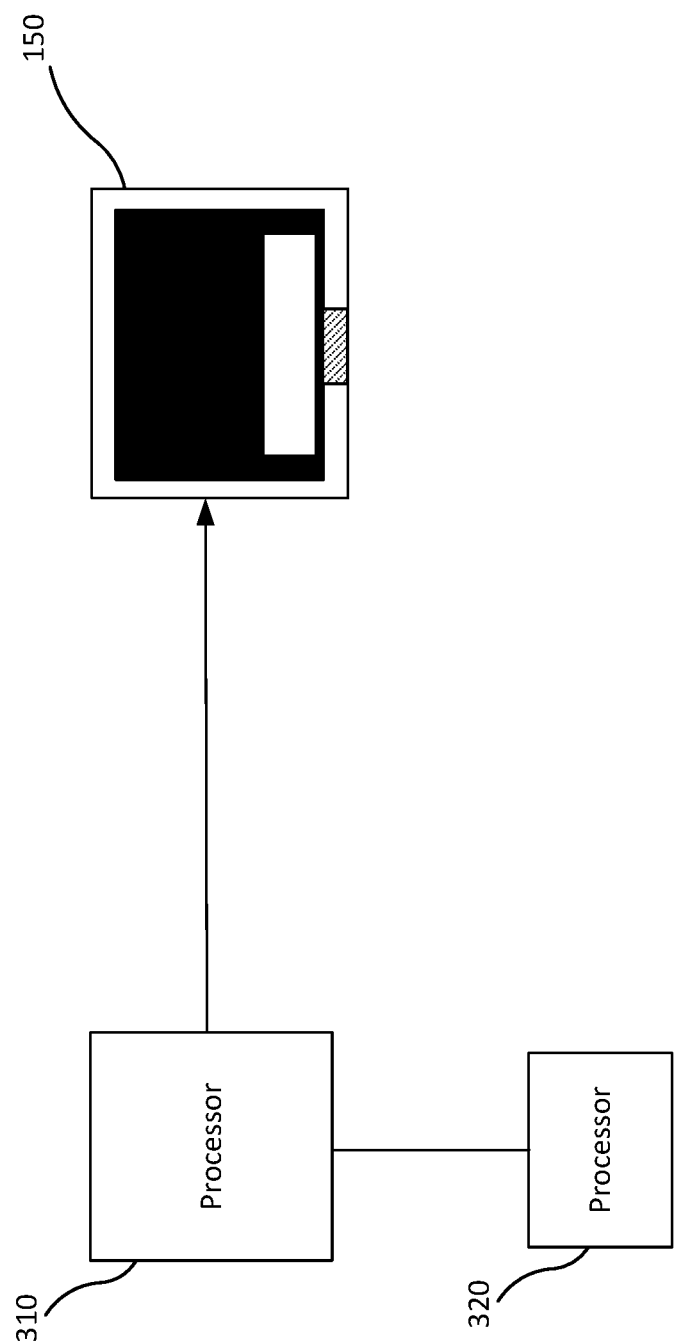
FIG. 3D illustrates a schematic diagram of an example system including the display device.

FIG. 3D illustrates a schematic diagram of an example system including the display device 150. In some embodiments, the cryogenic device 100 may include a first processor 310 that may be coupled to the display device. For example, the first processor 310 may be the first processor described above, which may be within the handpiece portion of the cryogenic device 100. In some embodiments, as illustrated in FIG. 3D, the cryogenic device 100 may also include a second processor 320 (e.g., the second processor described above, which may be associated with the needle probe 110) that may be coupled to the processor 310. The first processor 310 may be configured to generate user-interfaces that may be displayed on the display device 150. For example, the first processor 310 may generate an initial user-interface for display on the display device 150. This initial user-interface may or may not be based on a state of the cryogenic device 100. In some embodiments, a display processor (not shown) may be used to separately handle display-related tasks. For example, the display device 150 may include a display processor for handling tasks such as rotation of a displayed user interface, scrolling of a displayed user interface, switching between two or more interfaces, or any other suitable tasks. Although the disclosure describes many of the functions being performed by an element described as "a processor," the term "processor" as used in this disclosure encompasses any number of processors.

In some embodiments, a processor (e.g., the processor 310) may be configured to determine a state of the cryogenic device 100. The processor 310 may determine that the cryogenic device 100 is in a first state. Each state may be associated with one or more indicators, and the processor 310 may determine a state of the cryogenic device 100 based on these indicators. For example, the processor 310 may receive or access sensor data (e.g., from one or more accelerometers on the cryogenic device 100) to determine an orientation of the cryogenic device 100, and the processor 310 may use this determined orientation to determine that the cryogenic device 100 is in a particular state. In this example, the processor 310 may determine that the cryogenic device 100 is in a charging state when it is determined that the cryogenic device 100 is in a horizontal orientation (e.g., in an orientation for docking the device to the charging device 330) and when a battery of the cryogenic device 100 is being charged. Alternatively, the processor 310 may determine that that the cryogenic device 100 is in a charging state simply upon detecting that the battery is being charged. As another example, the processor 310 may determine that the cryogenic device 100 is in a cycle state when it determines that cryogen is being released from a cryogen cartridge (e.g., as determined by one or more pressure sensors detecting a pressure change from the outflow of cryogen, one or more temperature sensors detecting a temperature decrease along a cryogen pathway from the flow of cryogen, one or more sensors detecting the actuation of an user-input element such as a button for cryogen release, etc.). As another example, the processor 310 may determine that the cryogenic device 100 is in an error state when an error has been determined (e.g., when a connection to a needle probe is faulty, when there is insufficient charge to perform a treatment cycle, etc.).

In some embodiments, a processor (e.g., the processor 310) may be configured to generate instructions for rendering a user-interface based on a determined state of the cryogenic device 100. For example, the processor 310 may determine that the cryogenic device 100 is in a first state, and then may generate instructions for rendering a first user-interface that is associated with the first state. In some embodiments, a user-interface may include an icon field and a status element. The icon field may include icons or other representations that visually indicate information associated with the cryogenic device 100 (e.g., cartridge information, needle probe information, battery information) or a selected cryotherapy program (e.g., information about a selected cryozone size to be created, a selected number of cycles to be applied, an icon or label identifying a particular selected cryotherapy program). The status element may include a textual description indicating a current status, a recommendation, or other relevant information associated with the cryogenic device 100 (e.g., cartridge information, needle probe information, battery information, error information) or a selected cryotherapy program (e.g., information about a selected cryozone size to be created, a selected number of cycles to be applied, a name of a particular selected cryotherapy program, treatment recommendations).

FIGS. 4A-4B illustrate two example standard user-interfaces 400, which may be associated with a standard state of the cryogenic device 100. Such a user-interface may be displayed on the display device 150 when it is determined that the cryogenic device 100 is in the standard state. The example standard user-interfaces 400 illustrated in FIGS. 4A-4B include an icon field 455 and a status element 450. In some embodiments, the standard user-interface may include one or more elements that indicate a battery status of the cryogenic device 100. For example, referencing the examples in FIGS. 4A-4B, the standard user-interface 400 may include an icon or other such representation (e.g., the battery indicator element 420) that visually indicates a current battery level of the cryogenic device 100. FIG. 4A depicts a battery indicator element 420 when the battery level is at 10%, and FIG. 4B depicts a battery indicator element 420 when the battery level is at 100%. Alternatively or additionally, the standard user-interface 400 may include a numerical representation, such as the numerical element 425, that indicates the current battery level (e.g., using a percent, a fraction, a decimal, an absolute number). In some embodiments, the standard user-interface 400 may include one or more probe descriptor elements indicating information about the needle probe. For example, referencing FIG. 4A, the standard user-interface 400 may include a probe descriptor element 410, which may be an icon or other such representation that may visually indicate that a needle probe 110 may be coupled with (e.g., inserted into) the cryogenic device 100 and may further indicate information about the needle probe 110 (e.g., visually indicating that the needle probe 110 is a five-needle probe).

FIG. 4A may also include a numerical descriptor (e.g., the number "60" in FIG. 4A) that may indicates an amount of time a cycle is to take (e.g., 60 seconds). In some embodiments, the sub-region of the user-interface where the probe descriptor elements (e.g., the probe descriptor element 410, the probe descriptor element 440) appear may be blank (alternatively, the probe descriptor elements may appear as dashed outlines, or as blinking icons) when a needle probe is not coupled to the cryogenic device 100. In some embodiments, the standard user-interface 400 may include a probe descriptor element 440 that may textually describe the probe (e.g., "5×9 mm," describing a five-needle probe with needles that may be 9 mm in length). In some embodiments, the standard interface 400 may include a cryogen status indicator. The cryogen status indicator may indicate an amount of cryogen from a cryogen cartridge that has been used or an amount of cryogen (e.g., usable cryogen) that is remaining in the cryogen cartridge. For example, referencing the examples in FIGS. 4A-4B, the cryogen status indicator 430 may be an icon or other such representation that may visually indicate an amount of cryogen from a cryogen cartridge that has been used or an amount of usable cryogen remaining in the cryogen cartridge. As another example (not shown), a cryogen status indicator may be a numerical indicator that numerically indicates an amount of cryogen that has been used or an amount of usable cryogen (e.g., in absolute values, as a percentage, etc.). In some embodiments, a user-interface may include a cycle counter element that indicates a number of treatment cycles remaining for a current cryogen cartridge (e.g., in which case, the cycle counter element may count down), or alternatively, a number of treatment cycles performed with the current cryogen cartridge (e.g., in which case, the cycle counter element may count up). For example, referencing FIGS. 4A-4B, the cycle counter element 435 may display the number "3" to indicate that three treatment cycles may be remaining for a particular cryogen cartridge (or that three treatment cycles may have been performed with the cryogen cartridge). In some embodiments, the cryogen status indicator 430 (and/or the cycle counter element 435) may appear empty (or e.g., read "0") and/or flash to indicate that the cryogen cartridge has been depleted or when the cryogen cartridge does not have sufficient cryogen for a treatment cycle.

In some embodiments, the standard user-interface 400 may include a status element. For example, referencing FIG. 4A, the status element 450 recommends recharging the battery. As another example, referencing FIG. 4B, the status element 450 indicates that the cryogenic device 100 is ready to perform a treatment cycle. As another example, if it is determined that the cryogenic device 100 is in an incorrect orientation for performing a treatment, the status element 450 may indicate as much with appropriate text (e.g., "Incorrect Orientation"). In some embodiments, the amount of text to be displayed in the status element 450 may exceed the number of characters that can reasonably fit within the status element at a given time. For example, minimum font size requirements or resolution limits of the display may require that the text content be repetitively scrolled through the status element 450 or broken into smaller messages that are alternately displayed in sequence.

Figure 5A:
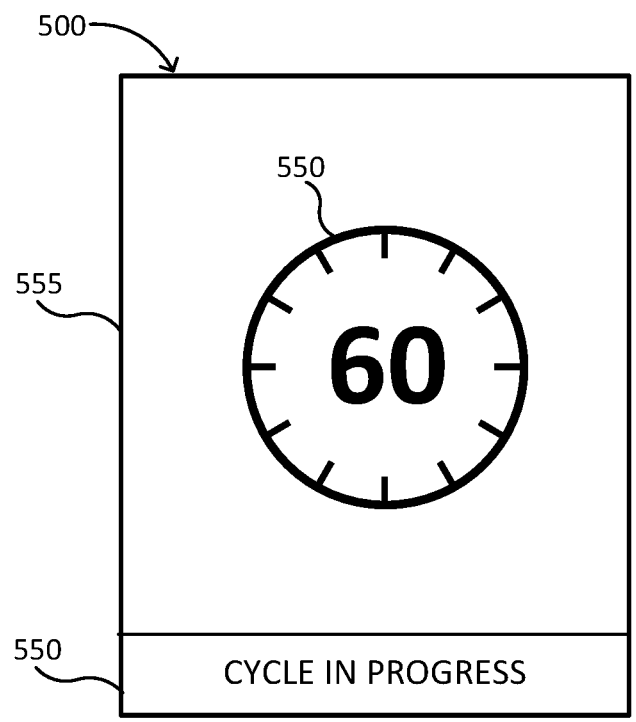
FIGS. 5A-5B illustrate two example cycle user-interfaces, which may be associated with a cycle state of the cryogenic device.
Figure 5B:
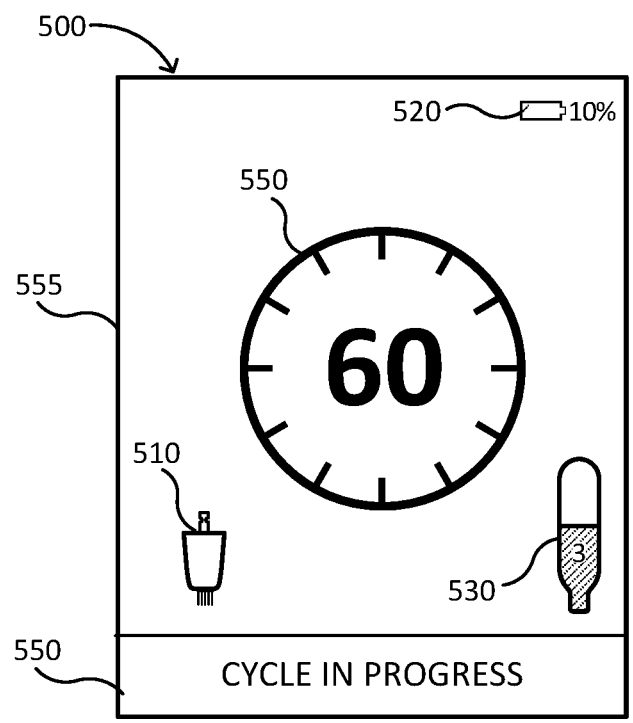

FIGS. 5A-5B illustrate two example cycle user-interfaces 500, which may be associated with a cycle state of the cryogenic device 100. The example standard user-interfaces 500 illustrated in FIGS. 5A-5B include an icon field 555 and a status element 550. In some embodiments, a cycle user-interface may include an enlarged progress element indicating a progress of a treatment cycle. For example, referencing FIGS. 5A-5B, the progress element 560 may be a visual representation of the progress of a current treatment cycle that may be in progress. In the illustrated example, the progress element 560 include a number (e.g., referencing FIGS. 5A-5B, the number "60") that may be a count-down or count-up timer indicating a number of seconds, minutes, or other suitable measurement of time. For example, an operator may begin a 60-second treatment cycle with the cryogenic device 100, in which case the example user-interface 500 in FIGS. 5A-5B may be presented, with the progress element 560 indicating 60 seconds. In this example, the number of the progress element 560 may the count down from 60 to 0 (e.g., at which point, the treatment cycle may be finished). Once a treatment cycle has been completed, the cycle user-interface 500 may be updated to indicate that the treatment cycle has been completed (e.g., via the status element 550). Alternatively, once the treatment cycle has been completed, the cycle user-interface 500 may be automatically transitioned to a different user-interface (e.g., the standard user-interface 400). The count-down or count-up may be alternatively or additionally indicated by a visual representation.

For example, the progress element 560 illustrated in FIGS. 5A-5B may include a clock hand modeled after a traditional analog timer that moves as the treatment cycle progresses to indicate remaining or elapsed time. As another example, a cycle user-interface 500 may include a linear progress bar, a circular progress bar, or other similar representation for visually showing progress of a treatment cycle. In some embodiments, as illustrated in FIG. 5B, the cycle user-interface 500 may also include other icons or representations showing other relevant information about the cryogenic device 100 or a selected cryotherapy program. For example, the icon field 555 may include a probe descriptor element 510, a battery status indicator 520, and a cycle counter element 530. In some embodiments, as illustrated in FIG. 5B, these other elements may be of reduced size relative to the progress element 560 when in the cycle user-interface 500. Displaying particular elements more prominently than other may be advantageous because, consistent with the goals of this disclosure, the most relevant information may be displayed most prominently for a given cryogenic device state such that this information is conveyed to the operator most effectively. For example, while a particular treatment cycle is in progress, the most relevant information may be the remaining or elapsed time for the particular treatment cycle. Although the interfaces illustrated in FIGS. 5A-5B display a progress element corresponding to an entire treatment cycle, this disclosure contemplates that similar interfaces may be shown for different phases of a treatment cycle. For example, an interface may show a progress element corresponding to a pre-treatment warming phase during a pre-treatment warming period, a progress element corresponding to a cooling phase during a cryogen delivery period, and a progress element corresponding to a recovery phase during a recovery period following the cryogen delivery period. In some embodiments, multiple progress elements for each phase of a treatment cycle may simultaneously be shown on a single interface (e.g., three progress elements for each of the three phases described in the previous example).

Figure 6A:
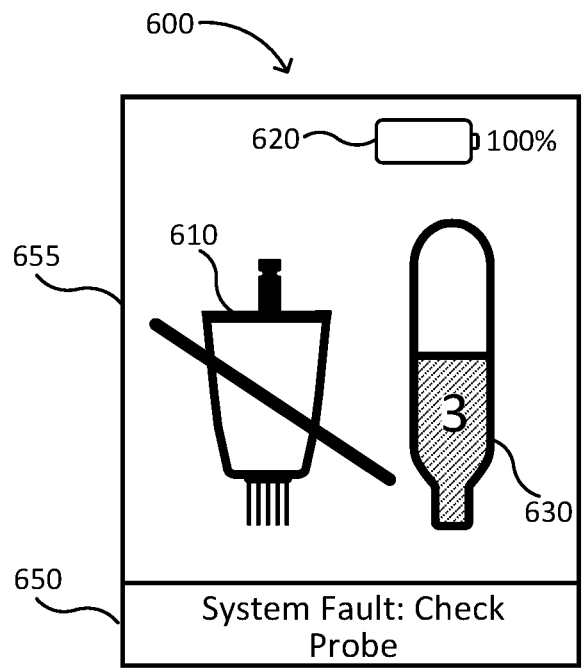
FIGS. 6A-6B illustrate two example error user-interfaces, which may be associated with an error state of the cryogenic device.
Figure 6B:
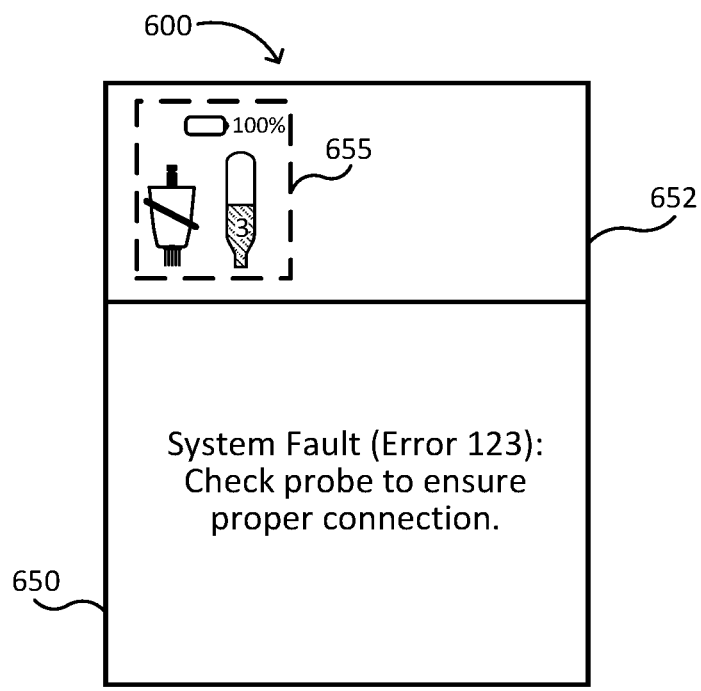

FIGS. 6A-6B illustrate two example error user-interfaces 600, which may be associated with an error state of the cryogenic device 100. The example standard user-interfaces 600 illustrated in FIGS. 6A-6B include an icon field 655 and a status element 650. In some embodiments, an error user-interface may be similar to a standard user-interface (e.g., the example standard user-interfaces 400 in FIGS. 4A-4B). For example, referencing FIG. 6A, the error user-interface 600 may include a battery status indicator 620, a probe descriptor element 610, a cycle counter element 630, and a status element 650. As illustrated, the status element 650 may include text describing an error and/or recommending an action to fix an error (e.g., "System Fault: Check Probe"). Additionally or alternatively, one or more elements in the icon field 655 may indicate an error. For example, referencing FIG. 6A, the probe descriptor element 610 has a strike-through line running through it, which may indicate that there is a problem with a needle probe connection (e.g., the needle probe may not be inserted into the cryogenic device 100 all the way). In other embodiments, the error user-interface may have an enlarged status element. For example, referencing FIG. 6B, the status element 650 in the error user-interface 600 has been enlarged. In this example, enlarging the status element 650 makes it more prominent, and also allows it to be used to convey detailed information for rectifying an error. The status element 650 in FIG. 6B includes an error code ("Error 123") and a detailed recommendation for rectifying the error ("Check probe to ensure proper connection"). As illustrated in FIG. 6B, in some embodiments, a reduced-size icon field 655 may be displayed (e.g., within a portion or region 652 of the error user-interface that does not overlap with the portion or region of the error user-interface dedicated to the status element 550). In some embodiments, an error user-interface may not include an icon field (e.g., the error-user interface may only include a large status element 650 that takes up the entire display screen or almost the entire display screen).

Figure 7A:
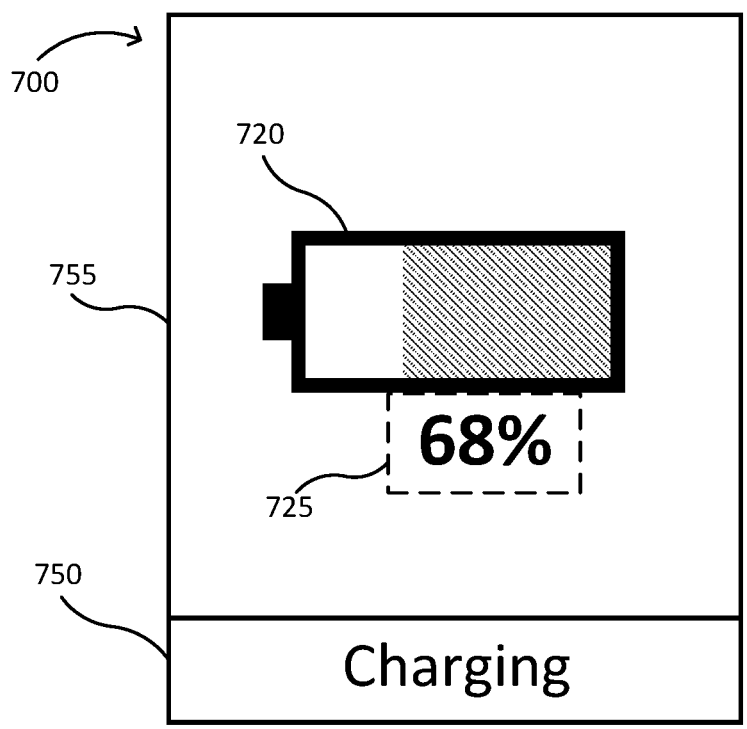
FIGS. 7A-7B illustrate two example charging user-interfaces, which may be associated with a charging state of the cryogenic device.
Figure 7B:
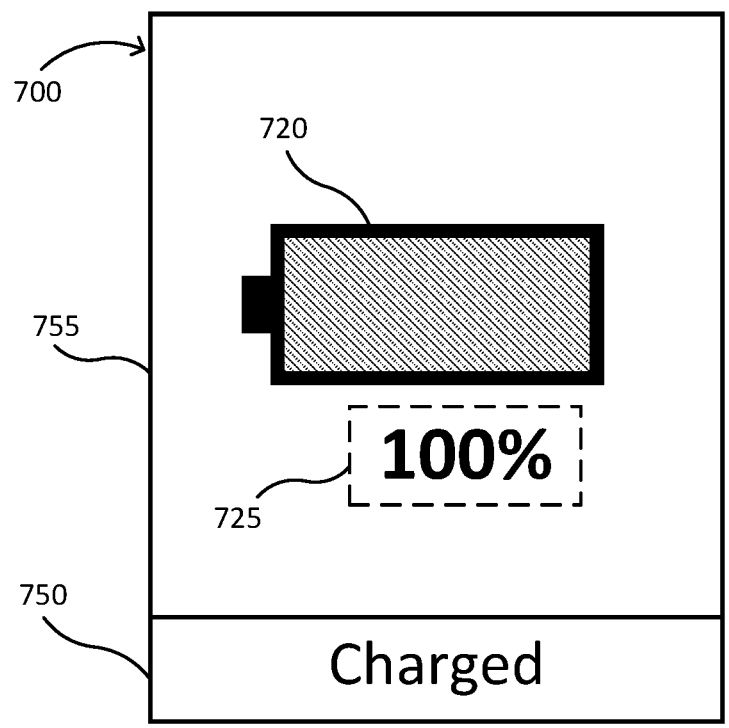

FIGS. 7A-7B illustrate two example charging user-interfaces 700, which may be associated with a charging state of the cryogenic device 100. As illustrated in FIGS. 7A-7B, the charging user-interface may include an icon field 755 and a status element 750. As illustrated, the icon field 755 may include an enlarged battery status indicator 720. Also as illustrated, the icon field 755 may include an enlarged numerical representation, such as the numerical element 725, that indicates a current battery level (e.g., using a percent, a fraction, a decimal, an absolute number). The battery status information is featured prominently (e.g., with the battery status indicator 720 and/or the numerical element 725) in the charging user-interface 700, so that an operator is able to quickly determine what may be the most relevant information while the device is charging—the battery level. The icon field may include icons or other representations that visually indicate information associated with the cryogenic device 100 (e.g., cartridge information, needle probe information, battery information) or a selected cryotherapy program (e.g., information about a selected cryozone size to be created, a selected number of cycles to be applied, and icon or label identifying a particular selected cryotherapy program). In some embodiments, the status element 750 may include a textual description indicating a current battery level (e.g., a percentage) or a status (e.g., the statuses "charging" and "charged," as illustrated in FIGS. 7A-7B).

In some embodiments, one or more elements of user-interfaces may be color-coded based on the information that they convey. For example, a status element that is colored green may indicate that the cryogenic device 100 is ready and does not require any further attention by the operator (e.g., when the status element is indicating that the cryogenic device is ready for treatment, that battery is charged, etc.). A status element that is colored yellow may indicate an alert that requires attention by the operator (e.g., when the status element is indicating that the battery needs to be recharged). A status element that is colored red may indicate that there is a system fault (e.g., when the needle probe is faulty, or when battery is so far beneath a threshold of the device is not operational). As another example, the battery status indicator may be color-coded based on the battery level. For example, the battery status indicator may be gray normally, flashing yellow if in a low-battery state, and flashing only an outline of the battery if in a depleted-battery state. As another example, the battery status indicator may be green normally, yellow if in a low-battery state, and red if in a depleted-battery state. In some embodiments, the entire background may be color-coded (e.g., green, yellow, and red, similar to the status element).

In some embodiments, the user-interfaces may be configured such that the contents are legible from 20 inches at viewing angles up to 45° and that light levels ranging from, for example, 150 to 1500 lux (for an operator with vision corrected to 20/20). The display device 150 may be of any suitable size and quality. For example, the display device 150 may be a 1.8-inch screen, with a resolution of 128×160 pixels, and a color palette of 4K or 64K colors.

In some embodiments, a processor such as the processor 310 may render a particular user-interface (e.g., one of the user-interfaces described herein) for display on the display 150. The display device 150 may display the particular user-interface (e.g., a standard user-interface, a cycle user-interface, a charging user-interface, an error user-interface). As is evident from the disclosure, the processor 310 may dynamically alter the user-interface that is displayed on the display device 150 based on a determined state of the cryogenic device 100 by transitioning between user-interfaces as appropriate.

In some embodiments, the orientation of a particular user-interface that is being displayed on the display device 150 may be dynamically altered based on a determined orientation of the cryogenic device 100. For example, as described elsewhere herein, the processor 310 may receive sensor data from an accelerometer and may use this sensor data to determine an orientation of the cryogenic device 100. The cryogenic device 100 may orient a user-interface based on the determined orientation, e.g., such that the user-interface is always displayed in a correct orientation. In other embodiments, the orientation of user-interfaces displayed on the display device 150 may be fixed, such that the user-interfaces always have the same orientation with respect to the display device 150 (irrespective of a determined orientation of the cryogenic device 100). This fixed orientation may encourage usage of the device in a particular (e.g., optimal) orientation, by indicating to an operator what the "correct" orientation is for using the cryogenic device 100. In some embodiments, particular user-interfaces may have particular orientations (again, irrespective of the determined orientation of the cryogenic device 100). For example, the standard user-interface 400, the cycle user-interface 500, and the error user-interface 600 may always be in a first orientation with respect to the display device 150, while the charging user-interface 700 may always be in a second orientation (e.g., a 180-degree rotation of the first orientation). As illustrated by this example, some user-interfaces may have optimal orientations that are different from other user-interfaces. This may be due to conditions associated with a cryogenic device state corresponding to the user-interfaces. Building on the previous example, when the cryogenic device 100 is properly docked onto the charging device 330 (as illustrated in FIGS. 3A-3B), the display device 150 may be in an upside-down orientation as compared to the orientation of the display device 150 during use. Accordingly, by orienting the charging user-interface 700 differently (e.g., an orientation having a 180-degree rotation from the orientation of other user-interfaces such as the standard user-interface 400), when an operator views the display device 150 as it is being charged, the charging user-interface 700 will be in a manner consistent with the orientation of the cryogenic device 100, so that the interface appears to be right-side up.

Figure 8:
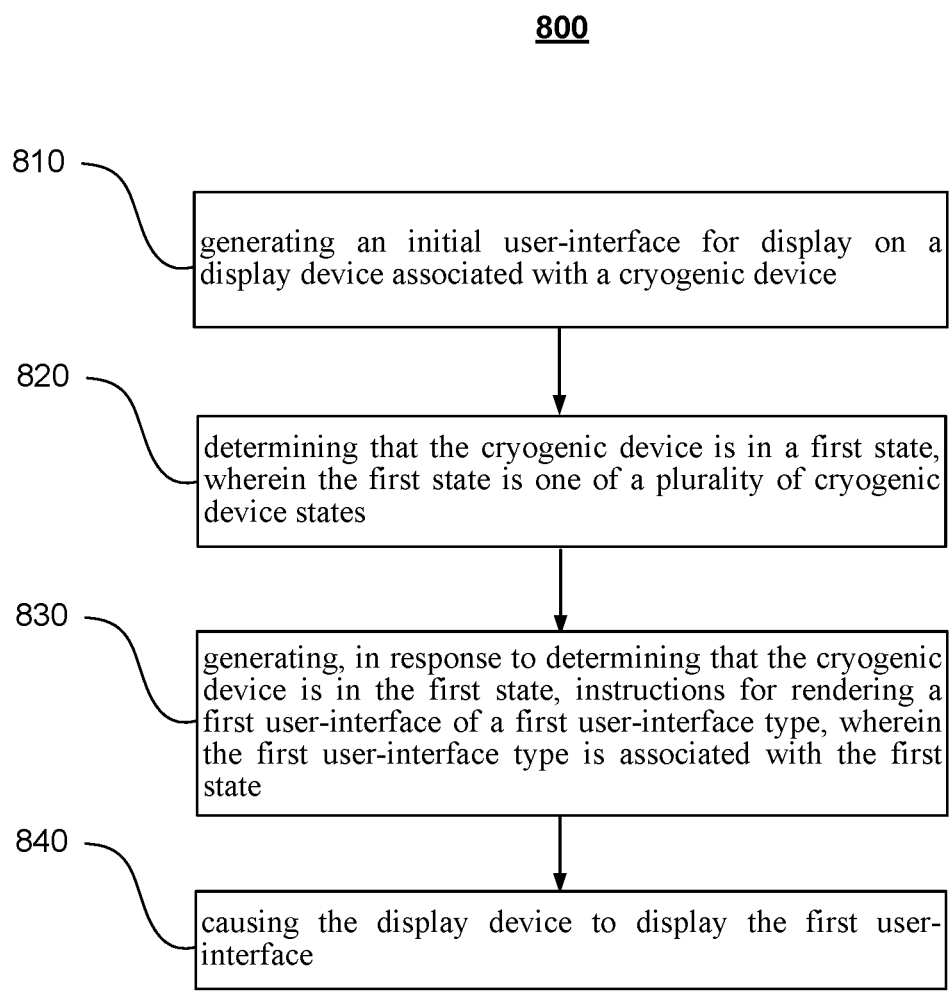
FIG. 8 illustrates an example method for displaying a dynamic user interface on a cryogenic device.

FIG. 8 illustrates an example method 800 for displaying a dynamic user interface on a cryogenic device. The method may begin at step 810, where a processor associated with the cryogenic device may generate an initial user-interface for display on a display device associated with the cryogenic device. At step 820, the processor may determine that the cryogenic device is in a first state, wherein the first state is one of a plurality of cryogenic device states. At step 830, the processor may generate, in response to determining that the cryogenic device is in the first state, instructions for rendering a first user-interface, wherein the first user-interface is associated with the first state and is one of a plurality of user-interfaces. At step 840, a processor may cause the display device to display the first user-interface. Particular embodiments may repeat one or more steps of the method of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for displaying a dynamic user interface on a cryogenic device, including the particular steps of the method of FIG. 8, this disclosure contemplates any suitable method for displaying a dynamic user interface on a cryogenic device, including any suitable steps, which may include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8.

While the exemplary embodiments have been described in some detail for clarity of understanding and by way of example, a number of modifications, changes, and adaptations may be implemented and/or will be obvious to those as skilled in the art.

What is claimed is:
1. A cryogenic device comprising:
a handpiece capable of being held by a user, the handpiece comprising a cryogen pathway configured to conduct a cryogen toward a needle probe comprising one or more needles configured for insertion into a skin of a patient, wherein the cryogen is configured to deliver cryotherapy to a target tissue via the one or more needles;

a display device configured to display one of a plurality of user-interfaces, the plurality of user-interfaces being associated with a plurality of cryogenic device states; and a processor coupled to the display device, wherein the processor is configured to:
generate an initial user-interface for display on the display device;
determine that the cryogenic device is in a standard state;
generate, in response to determining that the cryogenic device is in the standard state, instructions for rendering a standard user-interface, wherein the standard user-interface is associated with the standard state; and
cause the display device to display the standard user-interface, wherein the standard user-interface comprises an icon field indicating information associated with the cryogenic device and cryotherapy treatment, wherein the icon field comprises a cryogen status icon indicating an amount of usable cryogen for the cryotherapy treatment in a current cryogen cartridge, a battery icon indicating a battery status for the cryotherapy treatment, a probe descriptor icon indicating information about the needle probe for the cryotherapy treatment, and a status element for indicating a status of the cryogenic device and the cryotherapy treatment, wherein the cryogenic status icon, the battery icon, the probe descriptor icon, and the status element are displayed on the standard user-interface at the same time.

2. The cryogenic device of claim 1, wherein the display device is disposed on the handpiece, wherein the display device comprises an LCD or OLED screen.

3. The cryogenic device of claim 1, wherein the cryogen status icon of the standard user-interface indicates information associated with a selected cryotherapy program, wherein the selected cryotherapy program specifies a desired cryozone treatment volume or a number of cryotherapy treatment cycles on the cryogen status icon.

4. The cryogenic device of claim 1, wherein the plurality of cryogenic device states comprises:
a cycle state, wherein the cycle state is associated with the cryogenic device preparing for or performing a particular cryotherapy cycle of the cryotherapy treatment;
a charging state, wherein the charging state is associated with a battery of the cryogenic device being charged; and
the standard state associated with the cryogenic device being turned ON and not in the cycling state or the charging state.

5. The cryogenic device of claim 4, wherein:
the cycle state is associated with a cycle user-interface, wherein the cycle user-interface comprises an enlarged progress element indicating a progress of a treatment cycle during performance of the cryotherapy treatment; and
the charging state is associated with a charging user-interface, wherein the charging user-interface comprises an enlarged battery indicator element.

6. The cryogenic device of claim 5, wherein the cycle user-interface further comprises the status element.

7. The cryogenic device of claim 5, wherein the enlarged progress element comprises a count-down timer or a count-up timer.

8. The cryogenic device of claim 5, wherein the cycle user-interface and the standard user-interface are in a first orientation, and wherein the charging user-interface is in a second orientation, the first orientation being different from the second orientation, wherein the first orientation comprises a 180-degree rotation of the second orientation.

9. The cryogenic device of claim 5, wherein the processor is further configured to:
receive data from one or more accelerometers of the cryogenic device;
determine, based on the received data, an orientation of the cryogenic device; and
orient the standard user-interface in a manner consistent with the orientation of the cryogenic device.

10. The cryogenic device of claim 1, wherein the plurality of cryogenic device states comprises an error state associated with an error user-interface, wherein the error user-interface comprises a first portion comprising an icon indicating a particular error and a second portion comprising an enlarged status element indicating the particular error, wherein the first portion and the second portion are non-overlapping portions of the error user-interface.

11. The cryogenic device of claim 1, wherein the cryogen status icon further comprises a numerical indicator indicating a number of treatment cycles remaining for the cryotherapy treatment, wherein the cryogen status icon does not include the numerical indicator when the current cryogen cartridge is depleted.

12. The cryogenic device of claim 1, wherein the probe descriptor icon blinks when the needle probe is not coupled to the cryogenic device.

13. The cryogenic device of claim 1, wherein the status element indicates that the cryogenic device is in an incorrect orientation for performing the cryotherapy treatment.

14. A method of displaying a dynamic user interface on a cryogenic device comprising a cryogen pathway configured to conduct a cryogen toward a needle probe comprising one or more needles configured for insertion into a skin of a patient, wherein the cryogen is configured to deliver cryotherapy to a target tissue via the one or more needles, the method comprising, by a processor associated with the cryogenic device:
generating an initial user-interface for display on a display device associated with the cryogenic device;
determining that the cryogenic device is in a standard state, wherein the standard state is one of a plurality of cryogenic device states;
generating, in response to determining that the cryogenic device is in the standard state, instructions for rendering a standard user-interface, wherein the standard user-interface is associated with the standard state and is one of a plurality of user-interfaces, wherein the standard user-interface comprises an icon field indicating information associated with the cryogenic device and cryotherapy treatment, wherein the icon field comprises a cryogen status icon indicating an amount of usable cryogen in a current cryogen cartridge, a battery icon indicating a battery status, a probe descriptor icon indicating information about the needle probe, and a status element for indicating a status of the cryogenic device, wherein the cryogen status icon further includes a cycle counter element thereon indicating a number of cryotherapy treatment cycles remaining or performed for the cryotherapy treatment; and
causing the display device to display the standard user-interface.

15. The method of claim 14, wherein the display device is disposed on a handpiece of the cryogenic device, wherein the display device comprises an LCD or OLED screen.

16. The method of claim 14, further comprising scrolling textual description through the status element or breaking the textual description into smaller messages that are alternately displayed in sequence.

17. The method of claim 14, wherein the plurality of cryogenic device states comprises:
a cycle state, wherein the cycle state is associated with the cryogenic device preparing for or performing a particular cryotherapy cycle of the cryotherapy treatment;
a charging state, wherein the charging state is associated with a battery of the cryogenic device being charged; and
the standard state associated with the cryogenic device being turned ON and not in the cycling state or the charging state.

18. The method of claim 17, wherein the plurality of user-interfaces comprises:
a cycle user-interface associated with the cycle state, wherein the cycle user-interface comprises an enlarged progress element indicating a progress of a treatment cycle during performance of the cryotherapy treatment; and
a charging user-interface associated with the charging state, wherein the charging user-interface comprises an enlarged battery indicator element.

19. The method of claim 18, wherein the cycle user-interface further comprises the status element.

20. The method of claim 18, wherein the enlarged progress element comprises a count-down timer or a count-up timer.

21. The method of claim 18, wherein the cycle user-interface and the standard user-interface are in a first orientation, and wherein the charging user-interface is in a second orientation, the first orientation being different from the second orientation, wherein the first orientation comprises a 180-degree rotation of the second orientation.

22. The method of claim 18, further comprising:
receiving data from one or more accelerometers of the cryogenic device;
determining, based on the received data, an orientation of the cryogenic device; and
orienting the standard user-interface in a manner consistent with the determined orientation of the cryogenic device.

23. The method of claim 14, wherein the plurality of cryogenic device states comprises an error state associated with an error user-interface, wherein the error user-interface comprises a first portion comprising an icon indicating a particular error and a second portion comprising an enlarged status element indicating the particular error, wherein the first portion and the second portion are non-overlapping portions of the error user-interface.

24. A method of displaying a dynamic user interface on a cryogenic device comprising a cryogen pathway configured to conduct a cryogen toward a needle probe configured for insertion into a skin of a patient, wherein the cryogen is configured to deliver cryotherapy to a target tissue via the needle probe, the method comprising:
displaying an initial user-interface on a display device disposed on a handpiece of the cryogenic device;
determining that the cryogenic device is in one of a plurality of cryogenic device states comprising a cycle state associated with the cryogenic device preparing for or performing a particular cryotherapy cycle of a cryotherapy treatment, a charging state associated with a battery of the cryogenic device being charged, and a standard state associated with the cryogenic device being turned ON and not in the cycling state or the charging state;
generating, in response to determining that the cryogenic device is in one of the plurality of cryogenic device states, instructions for rendering one of a plurality of user-interfaces, the plurality of user-interfaces comprising:
a cycle user-interface associated with the cycle state;
a charging user-interface associated with the charging state;
a standard user-interface associated with the standard state, wherein the standard user-interface comprises a probe descriptor element indicating characteristics of the needle probe, wherein the standard user-interface comprises an icon field indicating information associated with the cryogenic device and the cryotherapy treatment, wherein the icon field comprises a cryogen status icon indicating an amount of usable cryogen for the cryotherapy treatment in a current cryogen cartridge, a battery icon indicating a battery status for the cryotherapy treatment, a probe descriptor icon indicating information about the needle probe for the cryotherapy treatment, and a status element for indicating a status of the cryogenic device and cryotherapy treatment; and
causing the display device to display one of the plurality of user-interfaces.

25. The method of claim 24, wherein the probe descriptor element indicating characteristics of the needle probe comprises indicating a number of needles of the needle probe, a configuration of the number of needles, or lengths of the number of needles.

26. The method of claim 25, wherein the probe descriptor element comprises an icon to visually indicate the needle probe.

27. The method of claim 25, wherein the standard user-interface further comprises a cryogen status indicator indicating an amount of usable cryogen in a current cryogen cartridge.

28. The method of claim 24, wherein the plurality of cryogenic device states further comprises a stand-by state associated with a power-saving mode, wherein a brightness of the display device is reduced.

* * * * *